United States Patent [19]  [11] 4,043,340
Cepuritis  [45] Aug. 23, 1977

[54] DIAPER WITH REPOSITIONABLE TAB FASTENER

[75] Inventor: Talivaldis Cepuritis, Kenilworth, Ill.

[73] Assignee: Johnson & Johnson, New Brunswick, N.J.

[21] Appl. No.: 661,918

[22] Filed: Feb. 27, 1976

[51] Int. Cl.² .............................................. A41B 13/02
[52] U.S. Cl. .................................... 128/287; 128/284
[58] Field of Search ............ 128/287, 284, 286, 290 R

[56] References Cited
U.S. PATENT DOCUMENTS

| 3,810,472 | 5/1974 | Aldinger et al. | 128/287 |
| 3,853,129 | 12/1974 | Kozak | 128/287 |
| 3,862,634 | 1/1975 | Small | 128/284 |
| 3,951,149 | 4/1976 | Ness et al. | 128/287 |

Primary Examiner—Stephen C. Pellegrino

[57] ABSTRACT

A disposable diaper has an improved tape tab fastening means in which a first tape strip has a free end and a fixed end which is attached to the diaper. A transferable tape segment is provided with an adhesive coating on both faces thereof, and one face is adhesively but releasably attached to the free end. The free end is adapted to secure the diaper about an infant by adhesive attachment via the adhesive-coated face of the transferable tape segment. There is a higher peel strength between the transferable tape segment and the diaper than between the transferable tape segment and the free end to enable the free end to be detachable from and refastenable to the transferable tape segment for repositioning the diaper about the infant. A permanently attached built-in release means is also provided.

9 Claims, 6 Drawing Figures

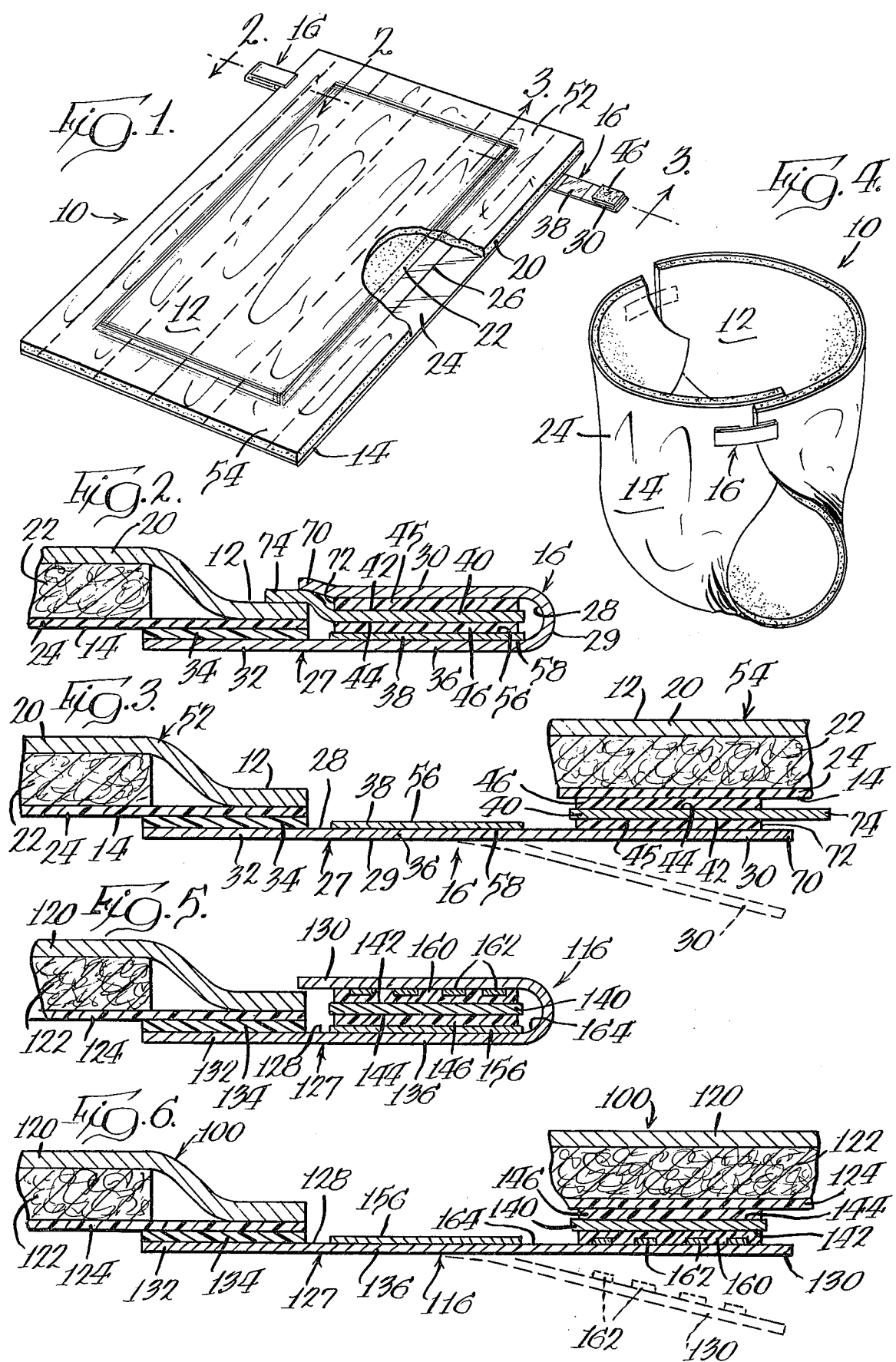

DIAPER WITH REPOSITIONABLE TAB FASTENER

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions which eliminate the need for pins, for example, which present problems especially when the infant is active during the diaper changing.

Although tape tab fastening means have become a suitable substitute for extraneous fasteners such as pins, a suitable tape tab fastening system has not been developed to simulate the ability of an extraneous fastener to be opened and subsequently closed. For example, when using pin fastening, if a diaper needs checking to see if the diaper has been soiled, the pin permits opening, and if no soiling is evident, the diaper is again closed about the infant repinning. Most prior tape tab systems have not provided this flexibility. The commercially available tape tabs which are used on disposable diapers cannot be broken readily to check for soiling or for repositioning the diaper. On most, if not all occasions undesirable rupture of the outside sheet of the diaper occurs or the tape tab itself is torn in order to check inside the diaper. This tearing has made refastening unmanageable or impossible and frequently results in the loss of a possibly unsoiled diaper.

In an attempt to solve the foregoing problems, U.S. Pat. No. 3,848,596 to Pennau teaches a tape tab fastening means which allows an originally fastened diaper to be opened and subsequently closed. The tape tab consists of two adhesive areas on each tab covered by two release sheets. On the first closure, only one release sheet is removed to expose pressure-sensitive adhesive. Upon adjustment or inspection, the tape is peeled from the fastened position, or the tab torn, and the other release sheet is removed, exposing fresh adhesive for a subsequent fastening. This arrangement is practical for only two fastenings, the original and one more and has the serious drawback that undesirable rupture of the diaper can occur when peeling off the tape tab if the diaper user does not choose to tear the tab itself. With a torn fastening area, refastening is very difficult even with a freshly exposed adhesive area on the tape.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two interconnected tape portions which cause the folded configuration of the sealing tape to be somewhat bulky.

SUMMARY OF THE INVENTION

According to the present invention, an improved economical tape tab system for use in disposable diapers permits an originally fastened diaper to be opened and reclosed several times without tearing the tape tab and without rupturing the diaper. Thus, the diaper can be opened and closed for inspection or adjustment during the normal service of the diaper as needed. The original closure and the subsequent closings around the infant provide a good, strong adhesive attachment of the diaper.

The disposable diaper has a facing sheet defining a diaper inside surface, a backing sheet defining a diaper outside surface and an absorbent layer positioned therebetween. A first tape segment has a fixed end secured to the diaper and a free end. The first tape segment has an inner face which faces in the same direction as the diaper inside surface when the first tape segment is in an extended position.

A double adhesive-faced transferable tape segment, relatively shorter than the first tape segment, is adhesively carried on the inner face of the free end. One face of the transferable tape segment is adhesively but releasably attached to an integral region which has release properties, and the opposite face of the transferable tape segment is provided with an adhesive coating. The free end of the first tape segment is folded over in a storage position so that the adhesive-coated opposite face of the transferable tape segment is releasably attached to the integral release means which can be carried on the diaper inside surface or on a midportion of the first tape segment.

The adhesive attachment of the one aforementioned face of the transferable tape segment to the free end of the first tape segment has a relatively higher peel strength than the attachment of the opposite adhesive-coated face of the transferable tape segment to the release means so that the free end and the transferable tape segment can be moved together from the folded-over position to an extended working position. The free end is adapted to secure the diaper about the infant by adhesive attachment to the diaper outside surface via the transferable tape segment. The adhesive attachment of the transferable tape segment to the diaper has a relatively higher peel strength than the adhesive attachment of the transferable tape segment to the free end to enable the free end to be detachable from and refastenable to the transferable tape segment for repositioning the diaper about the infant.

The improved tape tab system of the present invention will allow someone to inspect or adjust the diaper during the service of the diaper. Whereas many disposable diapers have to be discarded even when unsoiled because of torn tabs or rupture of the diaper, the improved system of the present invention provides the economical advantage of inspections and reuse of the diaper until soiled. Upon refastening, the tape tabs provide a good, strong securement to the diaper. Further features are the economy of manufacture, and a built-in release means which obviates the need for a removable cover strip.

BRIEF DESCRIPTION OF THE DRAWING

FIG. 1 is a perspective view, partially broken away to show interior detail, of an open unfolded diaper in accordance with the present invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3 and with the tab fastener attached to another region of the diaper, and showing in phantom the position which can be assumed by the detachable portion of the tab fastener of the present invention;

FIG. 4 is a perspective view of the diaper of FIG. 1 in a configuration assumed by the diaper when placed about an infant;

FIG. 5 is a fragmentary cross-sectional view similar to FIG. 2 and showing another embodiment of the invention in a folded-over position; and FIG. 6 is a fragmentary cross-sectional view similar to FIG. 3 and showing in solid lines the embodiment of FIG. 5 in an extended working position, and showing in phantom the position which can be assumed by the detachable portion of the tab fastener of the present invention.

DESCRIPTION OF THE PREFERRED EMBODIMENTS

In the following description, two digit numerals are used to refer to the embodiment of FIGS. 1-4 and three digit numerals in the one hundred series are used to refer to the embodiment of FIGS. 5 and 6. The same last two digits in each numeral designate similar elements in both embodiments.

Disposable diaper 10, illustrated in FIGS. 1 and 4, is of substantially quadrilateral configuration and presents inside surface 12 for direction toward an infant and outside surface 14 for direction away from the infant. Adhesive tab fastener means such as tabs 16 are attached to diaper 10 for securing diaper 10 about an infant. As described in greater detail below, tabs 16 are movable from a folded-over storage position illustrated in FIT. 2 to a working position which is illustrated in FIG. 3.

Referring to FIGS. 1-3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 and 3, adhesive tab 16 includes a first tape segment 27 having an inner face 28 and an outer face 29. Tape segment 27 has fixed end 32 permanently attached to diaper 10, preferably along outer surface 14, by means of adhesive coating 34 on inner surface 28 along fixed end 32, and free end 30 which includes midportion 36 adjacent to fixed end 32. Release means 38 is permanently attached to the diaper and is preferably provided on inner face 28 of midportion 36. Of course, release means 38 can be permanently attached to diaper facing sheet 20 and release-bearing midportion 36 can be omitted from the tab fastener, if desired. Adhesive coating 34 on fixed end 32 can be a pressure-sensitive adhesive composition, a heat-activated or solvent-activated adhesive composition, or the like.

Tab 16 further includes transferable tape segment 40 which is adhesively carried on inner face 28 of free end 30 and has first and second opposed faces 42, 44, provided with adhesive coatings 45, 46, respectively. First face 42 is directed towards first tape segment 27 and is adhesively but releasably attached to inner face 28 of free end 30 by means of adhesive coating 45. Second face 44 is adapted for adhesive attachment to diaper 10 by means of adhesive coating 46. As illustrated in FIG. 2, first tape segment 27 if folded about itself to assume a storage position wherein adhesive coating 46 on second face 44 of transferable tape segment 40 is releasably attached to release means 38 on inner face 28 of first tape segment 27, and the transferable tape segment 40 is substantially enveloped by first tape segment 27. Adhesive coatings 45, 46 preferably are a pressure-sensitive adhesive composition.

Pressure-sensitive adhesive coating 45 on transferable tape segment 40 provides a securement means which can be moved from the closed, storage position of FIG. 2 to the open working position of FIG. 3 for fastening the diaper about an infant. Adhesive coating 45 has a relatively higher peel strength vis-a-vis the contiguous first face 42 than the attachment of adhesive coating 46 on second face 44 to release means 38 carried on first tape segment 27 to thereby permit free end 30 of first tape segment 27 and the transferable tape segment 40 to be moved together from the folded-over position of FIG. 2, in which free end 30 is doubled over, to the extended working position of FIG. 3.

When tab 16 is in the extended working position of FIG. 3, free end 30 is adapted to secure diaper 10 about an infant by adhesive attachment to the outside surface 14 of the diaper via the transferable tape segment 40 which is carried by free end 30. The adhesive attachment of transferable tape segment 40 to diaper 10 has a relatively higher peel strength than the adhesive attachment of transferable tape segment 40 to free end 30 of first tape segment 37. Thus, while tape segment 40 remains attached to diaper 10 once diaper 10 is placed about an infant, free end 30 is detachable from and refastenable to transferable tape segment 40 for repositioning the diaper.

Diaper 10 can be fastened with tab 16 as depicted in FIG. 3. Fixed end 32 of first tape segment 27 is adhesively attached to corner 52 of diaper 10. When tab 16 is unfolded from the storage position of FIG. 2 to the working position of FIG. 3, tab 16 is adhesively fastened to an opposite corner 54 of diaper 10 by means of adhesive coating 46 on second face 44 of transferable tape segment 40. When the diaper is in the fastened condition, transferable tape segment 40 lies between first tape segment 27 and diaper outside surface 14. The fastening of first tape segment 27 to diaper 10 via transferable tape segment 40 provides a good, strong enclosure around the infant.

It is a feature of the present invention that when the diaper needs inspection or adjustment after an original closure has been made, first tape segment 27 can be peeled from transferable tape segment 40 because the peel strength between first tape segment 27 and transferable tape segment 40 is less than the peel strength between transferable tape segment 40 and diaper 10. Due to the difference in peel strengths, first tape segment 27 can be separated from transferable tape segment 40 and moved to the position illustrated in phantom in FIG. 3 to thereby open a fastened diaper without resorting to tearing the outside surface of the diaper or the tab itself. When first tape segment 27 is separated from transferable tape segment 40, fixed end 32 of first tape segment 27 remains secured to corner 52 of diaper 10 while the transferable tape segment 40 remains fastened to outside surface 14 of the opposite corner 54 of diaper 10 where the original closure was made. Once attached to outside surface 14, transferable tape segment 40 acts as a reinforcing agent by remaining on the diaper since the transferable tape segment adds strength to the area of the diaper which might otherwise tear upon peeling of first tape segment 27 from transferable tape segment 40 due to the stresses imposed on diaper 10 by the peeling action. When tape segments 27 and 40 are separated from one another, diaper 10 can be inspected for soiling and/or can be readjusted for a better or neater fit around the infant.

When the inspection and/or adjustment is completed, diaper 10 is wrapped around the infant as done originally and is refastened by positioning first tape segment 27 in an overlapping relationship with transferable tape segment 40 which remains attached to opposite corner 54 of diaper 10. Free end 30 of first tape segment 27 is pressed against adhesive coating 45 on first face 42 of transferable tape segment 40 to complete the closure. Since a portion of tape segments 27 and 40 in overlapping relationship will furnish a sufficient adhesive closure, there need not be a complete overlapping alignment between the two tapes upon subsequent refastenings.

In the embodiment illustrated in FIGS. 5 and 6, tab 116 is similar to tab 16 in FIGS. 1-4 and includes a first tape segment 127 and transferable tape segment 140. First and second faces 142 and 144 of transferable tape segment 140 are both provided with pressure-sensitive adhesive coatings 160, 146, respectively. A discontinuous layer 162 of release agent is provided on inner face 128 of free end 130 of first tape segment 127, preferably along the distal region of free working end 130, so that the discontinuous layer 162 of release agent preferably is spaced from midportion 136 of first tape segment 127 in order to provide a fresh surface 164 on free end 130 between midportion 136 and layer 162 of release agent for adhesion to transferable tape segment 140 upon repositioning of free end 130. If desired, fresh surface 164 can be embossed to increase the surface area thereof or otherwise treated to increase the adhesion between tape segments 127 and 140. Since first face 142 of transferable tape segment 140 is provided with adhesive coating 160, there is no need to provide an adhesive coating on free end 130 of the first tape segment 127. Discontinuous release layer 162 ensures that the peel strength between tape segments 127 and 140 is less than the peel strength between transferable tape segment 140 and diaper 100 to enable first tape segment 127 to be detached from and refastened to transferable tape segment 140 for repositioning diaper 10 about an infant.

It is a feature of both embodiments of the invention that free end 30, 130 of first tape segment 27, 127 does not carry any adhesive and therefore cannot stick to the user who is repositioning tab 16, 116, nor to other garments worn by the infant.

In the storage position, adhesive coating 46 on transferable tape segment 40 is releasably adhered to release means 38 which is substantially coextensive with adhesive coating 46. Release means 38 may comprise a ribbon segment or releases strip carried by midportion 36 and provided with a release coated face 56 which provides a release region, and an adhesive coating on opposite face 58 by means of which the release strip is anchored to midportion 36 of first tape segment 27. Alternatively, release means 38 may comprise a release coating, such as a silicone release compound or the like, on inner face 28 of midportion 36 of first tape segment 27 and is substantially coextensive with adhesive coating 46 on tape segment 40 when tab 16 is folded to the storage position. If desired, first tape segment 27 may be provided with a continuous pressure-sensitive adhesive coating on inner face 28 thereof, the portion of the adhesive coating along fixed end 32 being used to adhesively attach first tape segment 27 to diaper 10, the portion of the adhesive coating along free end 30 being adapted for attachment to transferable tape segment 40, and the portion of the adhesive coating along midportion 36 being covered by release means 38.

It is desirable to provide a gripping means to facilitate grasping tab 16 while moving from the folded-over storage position of FIG. 2 to the extended working position of FIG. 3, and to facilitate in separating first tape segment 27 from transferable tape segment 40. As shown in FIGS. 2 and 3, free end 30 can include projecting portion 70 which extends slightly beyond transverse edge 72 of adhesive coating 45, and transferable tape segment 40 can include integral grip tab means 74 adjacent to the distal portion of free end 30 and extending slightly beyond the distal portion of free end 30. A user can conveniently grasp grip tab means 74 to move tab 16 from the folded-over storage position to the extended working position. When it is desired to separate first tape segment 27 from transferable tape segment 40, the user can hold grip tab means 74 while simultaneously grasping projecting portion 70 while pulling free end 30 to separate tape segments 27 and 40.

The refastened diaper is provided with a strong adhesive attachment because the adhesive material comprising adhesive coatings 45, 160 remains after the original closure is broken. Repeated openings and closures of the diaper are possible.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 45 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd$^2$ and densities of less than 0.15 g./cc., generally in the range between 0.05 and 0.1 g./cc. The dry strength of the facing sheet for a fabric having a weight of about 1.5 oz./yd$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a nonapertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inches thick. Another suitable material for this purpose is a polyethylene terephthalate web having a thickness of about 0.0005 inches. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free end 30 of first tape segment 27 and transferable tape segment 40 away from the temporary engagement with release means 38, exposing adhesive coating 46 which was releasably adhered to release means 38. The tabs are then used to secure the diaper in the desired position by simply urging the pressure-sensitive adhesive surfaces in contact with the adjacent outer surface of the diaper, and can be detached and refastened as described hereinabove. The applied diaper assumes the configuration illustrated in FIG. 4.

The foregoing description and the drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:

a first tape segment having an inner face and an outer face and including a fixed end secured to the diaper, and a free end which includes a midportion of said first tape segment adjacent to said fixed end;

a transferable tape segment adhesively carried on the inner face of one portion of the free end and provided with an adhesive coating on opposing faces thereof, one adhesive-coated face being adhesively but releasably attached to said inner face of said one portion of the free end, and the other adhesive-coated face being adapted for adhesive attachment to said diaper; and release means permanently attached to said first tape segment along the remaining portion of said free end;

said free end being folded over to releasably attach said release means to the other of said opposed faces of said transferable tape segment and to substantially envelop said transferable tape segment between said midportion and said remaining portion of the free end of said first tape segment;

the adhesive attachment of said one face of said transferable tape segment to said free working end having a relatively higher peel strength than the attachment of said other adhesive-coated face to said release means to enable said free end and said transferable tape segment to be moved from the folded-over position to a working position in which said free working end is adapted to secure said diaper about said infant by adhesive attachment to said diaper outside surface via said transferable tape segment;

the adhesive attachment of said transferable tape segment to said diaper having a relatively higher peel strength than the adhesive attachment of said transferable tape segment to said free working end to enable said free working end to be detachable from and refastenable to said transferable tape segment for repositioning said diaper about said infant.

2. The disposable diaper as defined in claim 1 wherein said opposed faces of said transferable tape segment are both provided with a pressure-sensitive adhesive coating.

3. The disposable diaper as defined in claim 1 wherein said free working end is provided with a discontinuous layer of a release agent.

4. The disposable diaper as defined in claim 1 wherein said free end includes a midportion adjacent said fixed end and wherein said release means is a coating of a release agent on the inner face of said midportion and said free working end is doubled over to releasably attach said other of said opposed faces to said release means.

5. The disposable diaper as defined in claim 4 wherein said opposed faces of said transferable tape segment are both provided with a pressure-sensitive adhesive coating and wherein a discontinuous layer of release agent is provided on the distal region of said inner face on the free working end.

6. The disposable diaper as defined in claim 5 wherein said discontinuous layer of release agent is spaced from said midportion so as to provide on said free working end a fresh surface for adhesion to said transferable tape segment upon repositioning of said free working end.

7. The disposable diaper as defined in claim 6 wherein said fresh surface is embossed to increase the surface area thereof.

8. The disposable diaper as defined in claim 1 wherein said transferable tape segment is provided with an integral grip tab means adjacent to the distal portion of said free working end.

9. The disposable diaper as defined in claim 8 wherein said integral grip tab means extends beyond the distal portion of said free working end.

* * * * *